United States Patent [19]

McKendry et al.

[11] 4,116,672

[45] Sep. 26, 1978

[54] 4(3H)-OXOBENZO-2,1,3-THIADIAZINE-2,2-DIOXIDES AND DERIVATIVES THEREOF

[75] Inventors: Lennon H. McKendry, Midland, Mich.; Walter P. Bland, Silver Spring, Md.

[73] Assignee: The Dow Chemical Company, Midland, Mich.

[21] Appl. No.: 807,996

[22] Filed: Jun. 20, 1977

Related U.S. Application Data

[60] Division of Ser. No. 660,577, Mar. 12, 1976, Pat. No. 4,051,130, which is a continuation-in-part of Ser. No. 497,583, Aug. 15, 1974, abandoned, which is a continuation-in-part of Ser. No. 398,355, Sep. 17, 1973, abandoned.

[51] Int. Cl.$^2$ ............................................. A01N 9/14
[52] U.S. Cl. ............................................................. 71/91
[58] Field of Search ............................................ 71/91

[56] References Cited

U.S. PATENT DOCUMENTS

| 3,708,277 | 1/1973 | Zeidler et al. | 71/91 |
| 3,989,507 | 11/1976 | McKendry | 71/91 |

*Primary Examiner*—Catherine L Mills

[57] ABSTRACT

Disclosed are novel 4(3H)-oxobenzo-2,1,3-thiadiazine-2,2-dioxides and derivatives and methods employing the same in the control of undesired vegetation.

79 Claims, No Drawings

4(3H)-OXOBENZO-2,1,3-THIADIAZINE-2,2-DIOXIDES AND DERIVATIVES THEREOF

CROSS-REFERENCE TO RELATED APPLICATIONS

The present application is a division of pending prior application Ser. No. 660,577, filed Mar. 12, 1976, now U.S. Pat. No. 4,051,130 which in turn is a continuation-in-part of application Ser. No. 497,583, filed Aug. 15, 1974 now abandoned, which is in turn a continuation-in-part of our earlier application Ser. No. 398,355, filed Sept. 17, 1973, now abandoned.

BACKGROUND

The present invention relates to 4(3H)-oxo-benzo-2,1,3-thiadiazine-2,2-dioxides, derivatives thereof and methods for controlling unwanted plants with said compounds.

It is known that 3-(1-methylethyl)-1H-2,1,3-benzothiadiazin-4(3H)-one-2,2-dioxide and the salts thereof may be used as a herbicide. See U.S. Pat. Nos. 3,708,277 and 3,621,017. Related compounds having pharmacological activities are also known. See, for example, U.S. Pat. Nos. 3,217,001 and 3,041,336. The 3-(1-methylethyl)-1H-2,1,3-benzothiodiazin-4(3H)-one-2,2-dioxide compound is known to be useful in selective weed control in corn, sorghum, cereals, rice and turf. However, the action of such compound has not been found to be satisfactory in the control of weeds in the presence of certain desired broadleaf crops, such as cotton, since the compound has been found to exert a significant phytotoxic effect on the desired crop plants at dosage levels required for effective and economical weed control.

It is therefore an object of the instant invention to provide new valuable 4(3H)-oxobenzo-2,1,3-thiadiazine-2,2-dioxides and methods for the use thereof in the control of unwanted plants with negligible effect on the desired crop plants.

SUMMARY OF THE INVENTION

The present invention is directed to novel 4(3H)-oxobenzo-2,1,3-thiadiazine-2,2-dioxide compounds and derivatives thereof corresponding to the formula:

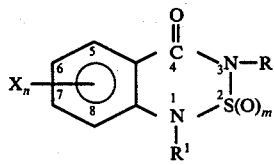

(I)

wherein:
each X independently represents loweralkyl, haloloweralkyl, cycloalkyl, aryl, —SCN, —COOR$^5$,

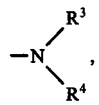

—YR$^2$, —SO$_2$R$^5$, —SO$_2$NR$^3$R$^4$, —CF$_3$;

or —YCF$_2$C(Z)$_3$;

$n$ represents an integer of 1 to 4, inclusive;
$m$ represents an integer of 1 to 2;
R represents loweralkyl, haloloweralkyl, alkenyl, haloalkenyl, alkynyl, haloalkynyl, cycloalkyl, phenyl, loweralkyl phenyl, halophenyl, benzyl, lowerakyl benzyl, halobenzyl, loweralkoxyloweralkyl, diloweralkylaminoloweralkyl; loweralkylthioloweralkyl; or cyanoloweralkyl;
R$^1$ represents hydrogen,

—SO$_2$R$^{10}$ or —SO$_2$NR$^8$R$_9$;
R$^2$ and R$^5$ each represent alkyl of 1 to 2 carbon atoms;
R$^3$ represents lower alkyl;
R$^4$ represents hydrogen or loweralkyl;
R$^6$ represents alkyl and haloalkyl each having 1 to 5 carbon atoms, alkenyl and haloalkenyl, each of 2 to 5 carbon atoms, cycloalkyl of 3 to 6 carbon atoms, lower alkoxyloweralkyl and loweralkylthioloweralkyl each of 2 to 6 carbon atoms, alkoxycarbonylalkyl of 4 to 8 carbon atoms, phenyl, loweralkylphenyl or halophenyl;
R$^7$ represents alkyl of 1 to 7 carbon atoms, haloalkyl of 1 to 4 carbon atoms, alkenyl and haloalkenyl of 3 to 6 carbon atoms, cycloalkyl of 3 to 6 carbon atoms, phenyl, loweralkylphenyl or halophenyl;
R$^8$ represents loweralkyl of 1 to 4 carbon atoms, and cycloalkyl of 3 to 6 carbon atoms; and when taken together with R$^9$ and the nitrogen from which each depends, a heterocyclic ring of 4 to 8 carbon atoms;
R$^9$ represents R$^8$ and alkoxy;
R$^{10}$ represents alkyl and haloalkyl, each of 1 to 7 carbon atoms;
each Y, Y' and Y'' independently represents a chalcogen group having an atomic number of from 8 to 16 inclusive;
each Z independently represents hydrogen, bromo, chloro or fluoro; and
where R$^1$ is hydrogen, the salts thereof with organic or inorganic bases.

The method of the present invention of selectively controlling undesired vegetation in the presence of desirable crop plants comprises applying a herbicidally effective amount of the above represented compounds to the area where control is desired.

For the sake of brevity and simplicity, the term "active ingredient(s)" is used hereinafter in this specification to broadly describe the novel 4(3H)-oxobenzo-2,1,3-thiadiazine-2,2-dioxide compounds and derivatives thereof.

DETAILED DESCRIPTION

The active ingredients of the present invention are useful as herbicides, particularly as post-emergent herbicides. Certain of the active ingredients of the present invention have unexpectedly been found to be suitable for controlling undesired vegetation in the presence of desired crops such as for example, cotton, without injuring the same. As used in the present specification and claims, the term "herbicide" means an active ingredient which, when used in a growth controlling amount, controls or modifies the growth of undesired plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant emerging seedlings and established vegetation, including the roots and above-ground portions.

The term "loweralkyl" is used herein and in the appended claims to designate a straight or branched chain alkyl or haloalkyl radical containing, where not otherwise expressly defined, from 1 to about 6 carbon atoms, such as, for example, methyl, ethyl, propyl, isopropyl, butyl, isobutyl, tert-butyl, pentyl, hexyl and the like.

The terms "halo" and "halogen", where employed herein, represent iodine, chlorine, fluorine and bromine. The term "cycloalkyl" is employed to mean radicals containing from 3 to about 8 carbon atoms, such as, for example, cyclopropyl, cyclobutyl, cyclopentyl, cyclohexyl, cyclooctyl and the like. The term "aryl" designates phenyl and substituted phenyl such as loweralkylphenyl, e.g., tolyl or xylyl, mono, di or trihalophenyl, and the like. The term "chalcogen" as used herein means those elements of the recognized chalcogen group having an atomic number of 8 to 16, inclusive, i.e, oxygen and sulfur.

The term "alkenyl" unless otherwise defined, as employed in the present specification and claims designates an alkenyl radical containing from about 3 to about 6 carbon atoms, inclusive, such as, for example, propenyl, 2-methyl propenyl, butenyl, hexenyl and the like which optionally may bear one or more halogen substituents. The term "alkynyl" as used herein and in the appended claims designated an alkynyl radical of from about 3 to about 6 carbon atoms, inclusive, such as, for example, propynyl, 2-methyl propynyl, butynyl, pentynyl, hexynyl and the like which optionally may bear one of more halogen substituents.

Those skilled in the art will appreciate the availability and possibility of substitution of the phenyl portion of the molecule corresponding to Formula I with substituents depicted by $X_n$ is limited only by the preselected values for X and n and steric considerations involved in placement of substituents about a molecule within a finite space.

If desired, compounds of Formula I, in which $R^1$ is hydrogen, can be converted into their salts with organic or inorganic bases.

The active ingredients of the present invention are liquids or crystalline solids at room temperature and are soluble in the usual organic solvents and somewhat soluble in water. The active ingredients of the instant invention are generally useful as herbicides. Certain of the active ingredients have been found to be particularly useful as selective post-emergent herbicides in the presence of cotton. In a preferred embodiment of this invention, X is loweralkyl of from one to about 4 carbon atoms. In a further preferred embodiment of the present invention, X is loweralkyl of from one to about four carbon atoms and is substituted in the 8-ring position, $n$ is 1, R is loweralkyl and $R^1$ is hydrogen,

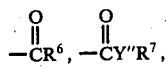

or $-SO_2R^{10}$. In another preferred embodiment, $n$ is 1 and X is loweralkyl of from 1 to about 2 carbon atoms and is substituted in the 8-ring position. In a further embodiment, compounds wherein R is isopropyl and $R^1$ is hydrogen,

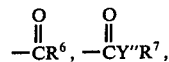

or $-SO_2R^{10}$, are preferred.

The active ingredients of the instant invention can be prepared by cyclising β-sulphamido carboxylic acid derivatives of the general formula:

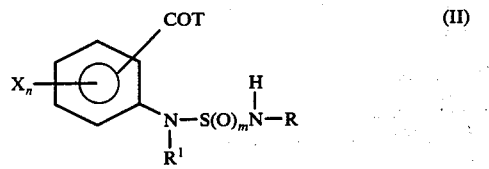

wherein X, $n$, $m$, Y, R and $R^1$ are as previously defined and T is a residue which is easily split off such as, for example, a hydroxy, alkoxy or aryloxy or halo group.

In carrying out the preparation of the compounds of the instant invention the selected β-sulphamido carboxylic acid can be cyclized to the desired corresponding active ingredient of the instant invention with a condensing agent. Representative examples of condensing agents include, for example, phosphorous oxychloride, thionyl chloride or aqueous or alcoholic alkaline solutions such as, for example, sodium methylate and the like. The reaction can be carried out under ambient atmospheric pressures and can be conducted in the presence of inert organic solvents such as, for example, benzene, toluene, xylene, higher ethers, halogenated hydrocarbons and the like. While the reactants can be employed in stoichiometric amounts, an excess amount of the condensing agent may also be employed.

The reaction is usually carried out at temperatures of from about 0° to about 150° C., and usually from about 5 to about 110° C. When T is alkoxy the cyclization can be conveniently accomplished in aqueous caustic at about 10 to about 30° C. or in alcoholic alkaline solutions at reflux temperature. The reaction is ordinarily completed in a period of from about 0.25 to 24 hours. The aqueous solution is extracted with an appropriate organic solvent and finally acidified to a pH of about 1.0 to about 3.0 to precipitate the desired product therefrom. Following the substantial completion of the reaction, the reaction mixture is cooled, acidified, and the solvent removed in vacuo. The residue thus obtained is extracted with a suitable solvent, such as, for example, carbon tetrachloride, methylene chloride, chloroform, cyclohexane, or the like, and the extracts combined and cooled to obtain the desired product as a crystalline solid. Alternatively, the solvent is removed prior to acidification and the residue obtained dissolved in water, extracted with ether, and the aqueous layer acidified to a pH of about 1.0 to about 3.0 to precipitate the desired product therefrom. If desired, the recovered product can be further purified by recrystallization from a suitable solvent such as hereinbefore mentioned.

The starting materials of formula II can be prepared according to known methods. Procedures for preparing the same as well as literature references to the same are provided in U.S. Pat. No. 3,041,336. Starting materials of Formula II wherein $R^1$ is hydrogen can, following cyclization as previously set forth, be converted to compounds where $R^1$ is other than hydrogen by reacting the same with most any of variously substituted halides of carbonic acid, carboxylic acids, sulphonic acids, sulfamic acids, carbamic acids, and other types of selected compounds corresponding to the meaning of $R^1$ set forth hereinbefore.

Such reactions can be performed in inert organic solvents such as hydrocarbons, halogenated hydrocarbons, alkanones, the dimethyl ether of ethylene glycol or the like and in the presence of alkali carbonates or bicarbonates. Starting materials of Formula II wherein X represents the —Y'CF$_2$C(Z)$_3$ moiety are readily prepared by known or analogous procedures disclosed in the literature. For example, starting materials of formula II, wherein X is —O(S)CF$_2$CHCl$_2$, are readily prepared by sparging 1,1-dichloro-2,2-difluoroethylene into a mixture of sodium methyl hydroxy(thiol)anthranilate in acetone at a temperature of from about 0° to about 10° C. for a period of about 1 to about 2 hours. Following the completion of the reaction, the solvent is removed by evaporation under reduced pressure and the desired starting material recovered. Those compounds wherein each Z is chloro or bromo are readily prepared by further photochemically halogenating the thus recovered starting material with an appropriate halogenating agent, such as, for example Cl$_2$, ClBr and the like in known procedures using a solvent such as carbon tetrachloride or a heterogeneous mixture employing water. Those starting materials wherein Z is fluoro are prepared by reacting the starting materials wherein Z is chloro or bromo with a molten antimony fluoro-chloro compound at temperatures of from about 80° to about 120° C. for periods of ½ to 2 hours. Other substituents in the 5, 6, 7 and 8 ring positions of the starting materials of Formula II may, depending upon the resistance of such substituent to the preceding reactions, be introduced after cyclization of the same to the corresponding 4(3H)-oxobenzo-2,1,3-thiadiazine-2,2-dioxide compound.

The following examples illustrate the present invention and the manner by which it can be practiced but, as such, should not be construed as limitations upon the overall scope of the same.

EXAMPLE 1

5-Thiocyanoanthranilic acid (8.5 grams; 0.52 mole) was dissolved in 300 milliliters (ml.) of benzene and isopropylsulfamoyl chloride (7 ml; 0.065 mole) added thereto. The resulting mixture was refluxed for a period of about 2 hours, cooled, and the solvent removed in vacuo. The resulting residue was suspended in 50 ml. of thionyl chloride and the resulting reaction mixture heated at the reflux temperature thereof for a period of about 3½ hours. Following the reaction period, the reaction mixture was cooled and evaporated in vacuo to obtain an oily residue which was extracted with four 100 ml. portions of carbontetrachloride and subsequently with two 100 ml. portions of methylene chloride. The extracts were combined and cooled to obtain the desired 6-isothiocyanato-3-(1-methylethyl)-1H-2,1,3-benzothiadiazin-4(3H)-one-2,2-dioxide product as a crystalline solid having a melting point of 169°–170.5° C. The recovered product was found to have carbon, hydrogen, nitrogen and sulfur contents of 44.70, 3.81, 14.07 and 21.9 percent, respectively, as compared with the theoretical contents of 44.44, 3.70, 14.14 and 21.55 percent, respectively, calculated for the named structure.

EXAMPLE 2

Methyl 3-methyl-2-((((1-methylethyl)amino)-sulfonyl)amino)benzoate (19.9 grams; 0.07 mole) and sodium methylate (7.5 grams; 0.14 mole) were mixed with 200 ml. of methanol and the resulting mixture heated at the reflux temperature thereof for a period of about four hours. The reaction mixture was then cooled and the methanol removed in vacuo. The resulting residue was dissolved in 200 ml. of water and the resulting solution extracted with 100 ml. of ether. The aqueous layer was then separated and acidified to a pH of about 2.0 with concentrated hydrochloric acid. The resulting precipitate formed upon acidification was recovered by filtration, dried and recrystallized from cyclohexane. As a result of these operations, the desired 8-methyl-3-(1-methylethyl)-1H-2,1,3-benzothiadiazin-4(3H)-one-2,2-dioxide compound was obtained as a crystalline solid having a melting point of 126.5°–127.5° C. and having carbon, hydrogen and nitrogen contents of 51.70, 5.63 and 11.15 percent, respectively, as compared with the theoretical contents of 51.93, 5.51 and 11.02 percent, respectively, calculated for the named structure.

EXAMPLE 3

To 100 ml benzene was added 30 g (0.182 mole) of methyl 3-methyl anthranilate and 28.05 ml (0.2 mole) of triethylamine. To the resultant solution was added dropwise 39.4 g. of 80% pure isopropylsulfamoyl chloride (0.2 mole) in 200 ml of benzene over a 2 hr period. The mixture was stirred 10 minutes and filtered to afford, upon drying in vacuo, 26.9 g of (C$_2$H$_5$)$_3$N.HCl. The solvent was removed from the filtrate in vacuo. The residue was washed once with cyclohexane to afford upon decantation and drying the residue in vacuo 56.6 g of gummy black solid identified by NMR as mainly desired intermediate methyl 3-methyl 2-((isopropyl)amino)sulfonyl)amino)benzamide.

The crude intermediate (55.6 g) was dissolved in 550 ml of 5% aqueous NaOH and the dark solution stirred 1 hour. The solution was titrated to pH=9 with concentrated HCl and extracted with three 100 ml-portions of CH$_2$Cl$_2$.

The aqueous layer was acidified to pH=1, stirred for 0.5 hour in an ice bath causing solidification of a precipitate, which was filtered off, and dried at 50° C in vacuo to afford 30.3 g of crude product containing ca 10% of 3-methyl anthranilic acid or its hydrochloride salt.

The tan solid was recrystallized from 300 ml of CCl$_4$ to afford 1.1 g of dark brown insoluble solid at reflux. The filtrate gave 25.0 g of 8-methyl-3-(1-methylethyl)-1H-2,1,3-benzothiadiazin-4(3H)-one-2,2-dioxide as tan crystals, m.p. 126°–129° C.

Other active ingredients of the instant invention are similarly prepared by employing procedures analogous to those set forth in Examples 1 through 3 above and the foregoing teachings of the specification by cyclizing a selected β-sulphamido carboxylic acid with a condensing agent. In addition the 1-substituted analogs such as those listed in the following table are prepared by causing the sodium or potassium salts of the thiadiazines in which $R^1$ is hydrogen to react with the appropriate halide in an invert solvent. Such other products corresponding to Formula I include the following:

TABLE I

| Cmpd. No. | X | Ring Position | R | R¹ | m | Melting Temperature, °C |
|---|---|---|---|---|---|---|
| 4 | —CH₃ | 7 | i-C₃H₇ | H | 2 | 159–161 |
| 5 | —OCH₃ | 8 | i-C₃H₇ | H | 2 | 113–114 |
| 6 | —CH₃ | 8 | i-C₃H₇ | —C(=O)—CH₃ | 2 | 103–104.5 |
| 7 | —CF₃ | 8 | i-C₃H₇ | H | 2 | 88–91 |
| 8 | —SO₂CH₃ | 8 | i-C₃H₇ | H | 2 | 139.5–140.5 |
| 9 | —CH₃ | 6 | i-C₃H₇ | H | 2 | 166–167 |
| 10 | —CH₃ | 8 | i-C₃H₇ | —C(=O)SC₃H₇ | 2 | ($n_D^{25}$ 1.5537) |
| 11 | —CH₃ | 8 | i-C₃H₇ | —C(=O)C₃H₇ | 2 | 82.84 |
| 12 | —CH₃ | 8 | i-C₃H₇ | —SO₂N(CH₃)₂ | 2 | 140–142 |
| 13 | —CH₃ | 8 | i-C₃H₇ | —C(=O)—SCH₃ | 2 | 110–112 |
| 14 | —CH₃ | 8 | i-C₃H₇ | —C(=O)—N(CH₃)₂ | 2 | 122–124 |
| 15 | —CH₃ | 8 | i-C₃H₇ | —C(=O)—O—C₃H₇ | 2 | 62.5–64 |
| 16 | —CH₃ | 8 | i-C₃H₇ | —SO₂C₃H₇ | 2 | 96–97 |
| 17 | —CH₃ | 8 | i-C₃H₇ | —C(=O)—OCH₃ | 2 | 116–118 |
| 18 | —CH₃ | 8 | i-C₃H₇ | —SO₂CH₃ | 2 | 168–170 |
| 19 | —C₂H₅ | 8 | i-C₃H₇ | H | 2 | 59–62 |
| 20 | —CH₃ | 8 | i-C₃H₇ | H | 2 | 126–129 |
| 21 | —SCH₃ | 8 | i-C₃H₇ | H | 2 | 93.5–94 |
| 22 | —SCN | 6 | i-C₃H₇ | H | 2 | 169–170.5 |
| 23 | —CH₃ | 8 | n-C₃H₇ | H | 2 | 96–97 |
| 24 | —CH₃ | 8 | —C₂H₅ | H | 2 | 91–93 |
| 25 | —CH₃ | 8 | —CH₃ | H | 2 | 109–110 |
| 26 | —CH₃ | 8 | n-C₄H₉ | H | 2 | 101–103 |
| 27 | —CH₃ | 8 | i-C₄H₉ | H | 2 | 108–110 |
| 28 | di—CH₃ | 7,8 | i-C₃H₇ | H | 2 | 154–157 |
| 29 | —CH₃ | 8 | 2-thienyl | H | 2 | 173.5–174.5 |
| 30 | —OCH₃ | 6 | i-C₃H₇ | H | 2 | 147.4–149 |
| 31 | —CF₃ | 7 | i-C₃H₇ | H | 2 | 212–214 |
| 32 | di—CH₃ | 6,8 | i-C₃H₇ | H | 2 | 141–143 |
| 33 | di—CH₃ | 5,8 | i-C₃H₇ | H | 2 | 170–171 |
| 34 | i-C₃H₇ | 8 | i-C₃H₇ | H | 2 | 121–123 |
| 35 | —CH₃ | 5 | i-C₃H₇ | H | 2 | 131–135 |
| 36 | —OCH₃ | 8 | s-C₄H₉ | H | 2 | 100.5–102.5 |
| 37 | —OCH₃ | 8 | n-C₃H₇ | H | 2 | 106–109 |
| 38 | —CH₃ | 8 | t-C₄H₉ | H | 2 | 115–116 |
| 39 | —CH₃ | 8 | i-C₃H₇ | —C(=O)C₃H₇ | 2 | 82–84 |
| 40 | —CH₃ | 8 | i-C₃H₇ | —C(=O)—O—n-C₄H₉ | 2 | 41.5–44 |
| 41 | —CH₃ | 8 | i-C₃H₇ | —SO₂—n-C₄H₉ | 2 | 79.5–81 |
| 42 | —CH₃ | 8 | i-C₃H₇ | —C(=O)—OC₂H₅ | 2 | 79–81 |
| 43 | —CH₃ | 8 | s-C₄H₉ | H | 2 | 109–112 |
| 44 | —CH₃ | 5,8 | —CH₂—CH₂Cl | H | 2 | |
| 45 | -n-C₃H₇ | 8 | —C₂H₄Cl | H | 2 | |
| 46 | —C₆H₁₁F₂ | 5 | -i-C₃H₇ | —H | 2 | |
| 47 | phenyl | 8 | -i-C₃H₇ | —H | 2 | |
| 48 | p-tolyl | 7 | —C₂H₅ | —H | 1 | |
| 49 | —CH₃ | 5,8 | —C₅H₁₀Cl | H | 1 | |
| 50 | —OCH₃ | 8 | -i-C₃H₇ | H | 1 | |
| 51 | —SC₆H₁₁ | 6 | —CH₃ | H | 2 | |
| 52 | 6-SCN, 8-CH₃ | 6,8 | —CH₂CH=CH₂ | —H | 2 | |
| 53 | 6-t-C₄H₉ | 6 | —CH₂C≡CH | H | 2 | |
| 54 | —COOCH₃ | 7 | —(CH₂)₄C≡CH | —SO₂CH₃ | 2 | |
| 55 | —CF₃ | 6 | -i-C₃H₇ | —CO₂-n-C₄H₉ | 2 | |
| 56 | CF₃ | 6 | -n-C₆H₁₃ | H | 2 | |
| 57 | 5-CH₂Cl, 7-SC₃H₅ | 5,7 | —CH₂CH₃ | H | 2 | |
| 58 | 5-CH₃, 8-OC₃H₇ | 5,8 | -i-C₃H₇ | —SO₂CH₃ | 2 | |
| 59 | 5-NHC₆H₁₁, 8-CH₃ | 5,8 | —CH₂CH=CHCl | H | 2 | |
| 60 | —C(=O)—C₆H₁₁ | 6 | —CH₃ | H | 2 | |
| 61 | 6-cyclohexyl; 8-CH₂F | 6,8 | CH₂CH₂CH₃ | H | 2 | |
| 62 | —CH₃ | 5,6,7 | -i-C₃H₇ | H | 2 | |
| 63 | —SO₂C₆H₁₁ | 6 | cyclohexyl | H | 2 | |
| 64 | —CF₃ | 5,7 | —CH₂CH₂CH₃ | H | 2 | |
| 65 | —CF₃ | 5,7 | -cyclopropyl | H | 1 | |
| 66 | 6-SO₂N(C₂H₅)₂, 8-CH₃ | 6,8 | -i-C₃H₇ | H | 2 | |

TABLE I-continued

| Cmpd. No. | X | Ring Position | R | R¹ | m | Melting Temperature, °C |
|---|---|---|---|---|---|---|
| 67 | 6-SCN, 8-OCH$_3$ | 6,8 | —C$_2$H$_5$ | —CO$_2$CH$_3$ | 2 | |
| 68 | —CH$_2$CHF$_2$ | 6 | i-C$_3$H$_7$ | —SO$_2$-n-C$_3$H$_7$ | 2 | |
| 69 | OCF$_2$CHCl$_2$ | 8 | -i-C$_3$H | H | 1 | |
| 70 | —SCF$_2$CCl$_3$ | 6 | i-C$_3$H$_7$ | H | 2 | |
| 71 | 5-OCF$_2$CH$_2$F, 8-CH$_3$ | 5,8 | CH$_2$CH$_2$CH$_3$ | H | 2 | |
| 72 | 8-SCF$_2$CF$_3$ | 8 | —CH$_2$CH$_3$ | H | 1 | |
| 73 | CH$_3$ | 8 | —C(CH$_3$)$_2$C≡CH | H | 2 | |
| 74 | CH$_3$ | 8 | —C(CH$_3$)$_2$C≡N | H | 2 | |
| 75 | 5-CF$_3$ | 5 | —C(CH$_3$)$_2$C≡N | —COCH$_3$ | 2 | |
| 76 | 6-OCF$_2$CHCl$_2$ | 6 | —C(CH$_3$)$_2$C≡CH | —SO$_2$CH$_3$ | 2 | |
| 77 | OCH$_3$ | 8 | i-C$_3$H$_7$ | H | 2 | |
| 78 | CH$_3$ | 8 | cyclohexyl | H | 2 | |
| 79 | —CH$_3$ | 8 | sec. butyl | H | 2 | |
| 80 | —CH$_2$CH$_3$ | 8 | i-C$_3$H$_7$ | H | 2 | |
| 81 | —OCH$_3$ | 8 | —C$_2$H$_5$ | H | 2 | |
| 82 | —N(CH$_3$)$_2$ | 8 | i-C$_3$H$_7$ | H | 2 | |
| 83 | —OCH$_3$ | 5 | i-C$_3$H$_7$ | H | 2 | |
| 84 | CH$_3$ | 8 | sec. butyl | H | 2 | |
| 85 | CH$_3$ | 8 | phenyl | H | 2 | |
| 86 | CH$_3$ | 8 | tolyl | H | 2 | |
| 87 | CH$_3$ | 8 | —CH$_2$S—CH$_3$ | H | 2 | |
| 88 | CH$_3$ | 8 | —CH$_2$N(C$_2$H$_5$)$_2$ | H | 2 | |
| 89 | CH$_3$ | 8 | —CH$_2$— | H | 2 | |
| 90 | CH$_3$ | 8 | —CH$_2$—Cl | H | 2 | |

The compounds of the present invention have been found to be suitable for use in the post-emergent control of weeds or other unwanted vegetation. Unexpectedly, certain of the active ingredients of the present invention have been found to be active against undesired vegetation in the presence of desired cotton plants while producing only a negligible effect on the cotton plants. For such uses, unmodified active ingredients of the present invention can be employed. However, the present invention embraces the use of active ingredients with a material known in the art as an adjuvant in solid or liquid form. Thus, for example, an active ingredient can be dispersed on a finely divided solid and employed therein as a dust. Also, the active ingredients, or a solid composition comprising the active ingredients, can be dispersed in water, typically with the aid of a wetting agent, and the resulting aqueous suspension employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 5 to about 95 percent by weight or more. Concentrations of from about 5 to about 50 weight percent are often employed. In dusts or dry formulations, the concentration of the active ingredient can be from about 0.1 to about 95 weight percent or more; concentrations of from about 1 to about 50 weight percent are often conveniently employed. In compositions to be employed as concentrates, the active ingredient can be present in a concentration of from about 5 to about 98 weight percent. The active ingredient compositions can also contain other compatible additaments, for example, fertilizers, phytotoxicants, plant growth regulants, pesticides and the like.

The active ingredients are most usefully brought into commerce in the form of (1) a wettable powder in which one or more of the active ingredients in finely divided form are blended with one of the wetting agents or surfactants above listed with or without combination, also with a finely divided absorptive clay or other absorptive inert adjuvant or carrier as listed above; (2) a flowable concentrate which corresponds largely to a "pre-wet" wettable powder composition having as high as 50 percent solids content and containing water and/or other appropriate liquid as well understood in the formulation art and (3) an emulsifiable concentrate in which one or more of the active ingredients are dissolved in an organic solvent, such as one of those listed, in admixture with a wetting, dispersing, or emulsifying agent, such as those described above, whereby the concentrate will readily become an emulsion on dilution with water.

In general treating operations for the modification and control of vegetative growth, plants are contacted with sufficient amounts of a composition containing one or more active ingredients to provide a dosage rate of from about 0.1 to about 30 or more pounds of active ingredient per acre, preferably about 0.1 to about 10 pounds per acre. In selective post-emergent operations in the presence of desired cotton plants, the active ingredients are applied at a rate of from about 0.25 to about 4.0 pounds per acre. It is to be understood, however, that all of the active ingredients claimed and compositions containing the same may not be equally effective at similar concentrations against the same plant species.

The present compounds are particularly useful in selectively controlling undesired vegetative growth in the presence of soybean plants in post emergent operations in which the active ingredients are applied at a rate of from about 0.25 to about 4 pounds per acre, and preferably at a rate of from about 0.25 to 2 pounds per acre.

So as to illustrate clearly the phytotoxic properties of the active ingredients claimed herein, a group of controlled greenhouse experiments is described below.

Various species of plants (A-J below) were planted in beds of good agricultural soil in a greenhouse. After the plants had emerged and grown to a height of about 2–6 inches, a portion of the plants was sprayed with an aqueous mixture made by mixing the selected active ingredient and emulsifier or dispersant with water, employing sufficient amounts of the treating compositions to provide application rates of 0.5, 1.0 and 2.0 pounds per acre. Other portions of the plants were left untreated to serve as controls.

After a period of 2 weeks the effect of the 8-methyl-3-(1-methylethyl)-1H-2,1,3-benzothiadiazin-4(3H)-one-2,2-dioxide test ingredient (Compound 2 (a-c)) and the comparative test ingredient, 3-(1-methylethyl)-1H-2,1,3-benzothiadiazine-4(3H)-one-2,2-dioxide (Compound 1 (a-c)), on the plants was evaluated and the data set forth in the following Table II. The data show the selective superiority of the 8-methyl substituted derivative over the corresponding unsubstituted derivative.

TABLE II

| Cmpd. No. | Rate Lbs/Acre | Percent Post-Emergent Control of Plants ||||||||||
|---|---|---|---|---|---|---|---|---|---|---|
| | | A | B | C | D | E | F | G | H | I | J |
| 1a. | 2.0 | 100 | 100 | 100 | 100 | 100 | 100 | 100 | 100 | 100 | 100 |
| b. | 1.0 | 100 | 100 | 100 | 75 | 100 | 85 | 100 | 80 | 100 | 65 |
| c. | 0.5 | 100 | 100 | 100 | 55 | 100 | 60 | 100 | 35 | 70 | 30 |
| 2a. | 2.0 | 100 | 100 | 100 | 100 | 100 | 100 | 100 | 100 | 100 | 25 |
| b. | 1.0 | 100 | 100 | 100 | 100 | 100 | 75 | 100 | 100 | 100 | 10 |
| c. | 0.5 | 100 | 100 | 100 | 80 | 100 | — | 100 | 100 | 100 | 5 |

A = Cocklebur, B = Prickley Sida, C = Wild Mustard, D = Field Bindweed, E = Jimson Weed, F = Pigweed, G = Lambsquarter, H = Coffeeweed, I = Velvet Leaf, and J = Cotton
Compound 1 = 3-(1-methylethyl)-1H-2,1,3-benzothiadiazine-4(3H)-one-2,2-dioxide; Compound 2 = 8-methyl-3-(1-methylethyl)-1H-2,1,3-benzothiadiazin-4(3H)-one-2,2-dioxide--.

In additional operations employing the above procedures, 1H-2,1,3-benzothiadiazin-4(3H)-one-2,2-dioxide was found to give 0% control of the weed species wildoats, foxtail, barnyard grass, crabgrass, pigweed, bindweed and velvet leaf even at a high dosage rate of eight pounds per acre. In other similar operations, 6-isothiocyanato-3-(1-methylethyl)-1H-2,1,3-benzothiadiazin-4(3H)-one-2,2-dioxide gave 100% control of velvet leaf with no effect on cotton plants.

In further comparative operations employing the above described procedures and test ingredient dosage rates of one, one-half and one-fourth pounds per acre, respectively, it was found that 3,8-dimethyl-1H-2,1,3-benzothiadiazin-4(3H)-one-2,2-dioxide (Compound A) and 3-ethyl-8-methyl-1H-2,1,3-benzothiadiazin-4(3H)-2,2-dioxide (Compound B) were selectively active in completely controlling velvet leaf at low dosage rates of one-half and one-fourth pounds per acre, respectively, with negligible effect on cotton whereas 3-(1-methylethyl)-1H-2,1,3-benzothiadiazin-4(3H)-one-2,2-dioxide (Compound C) was significantly toxic to cotton and also failed to give good control of velvet leaf at such low dosage rates. The results of such tests are set forth below in Table III.

TABLE III

| Cmpd. No. | Dosage Rate lbs/Acre | % Control ||
|---|---|---|---|
| | | Velvet Leaf | Cotton |
| A | 1.0 | 100% | 45% |
| | 0.5 | 100% | 15% |
| | 0.25 | 100% | 0% |
| B | 1.0 | 100 | 25 |
| | 0.5 | 100 | 0 |
| | 0.25 | 100 | 0 |
| C | 1.0 | 100 | 65 |

TABLE III-continued

| Cmpd. No. | Dosage Rate lbs/Acre | % Control Velvet Leaf | Cotton |
|---|---|---|---|
| | 0.5 | 70 | 30 |
| | 0.25 | 45 | 10 |

In similar additional operations, 8-methyl-3-propyl-1H-2,1,3-benzothiadiazin-4(3H)-one-2,2-dioxide gave 100, 95 and 90% control of bindweed and 20, 15 and 0% control of cotton at dosage rates of one, one-half and one-fourth pounds per acre, respectively. By comparison, the 3-(1-methylethyl)-1H-2,1,3-benzothiadiazin-4(3H)-one-2,2-dioxide compound gave 75, 55 and 35 percent control of bindweed and 65, 30 and 10% control of cotton at such respective dosage rates, thus indicating the superior activity and safety of the 8-methyl-3-propyl-1H-2,1,3-benzothiadiazin-4(3H)-one-2,2-dioxide compound at low dosage rates.

In similar operations employing the foregoing procedures, each of the 8-ethyl-3-(1-methylethyl)-1H-2,1,3-benzothiadiazin-4(3H)-one-2,2-dioxide and 3-cyclohexyl-8-methyl-1H-2,1,3-benzothiadiazin-4(3H)-one-2,2-dioxide test ingredients gave substantially complete control of pigweed and velvet leaf at an application rate of about 10 pounds per acre while the 3-(1-methylethyl)-7-(trifluoromethyl)-1H-2,1,3-benzothiadiazin-4(3H)-one-2,2-dioxide test ingredient was found to give substantially complete control of the growth of pigweed and nutsedge at such application rate.

In other representative operations employing procedures as outlined above, each of the 8-methyl-3-(1-methylethyl)-1-(phenylsulfonyl)-1H-2,1,3-benzothiadiazin-4(3H)-one-2,2-dioxide and 7,8-dimethyl-3-(1-methylethyl)-1H-2,1,3-benzothiadiazin-4(3H)-one-2,2-dioxide test ingredients was found to give substantially complete control of the growth of velvet leaf at an application rate of about 10 pounds per acre. No adverse growth effects to cotton plants were observed with either test ingredient at such application rate.

In still other such representative operations, the respective 8-methoxy-3-(1-methylethyl)-1H-2,1,3-benzothiadiazin-4(3H)-one-2,2-dioxide and 8-methyl-3-(1-methylpropyl)-1H-2,1,3-benzothiadiazin-4(3H)-one-2,2-dioxide test ingredients were found to give substantially complete control of velvet leaf and pigweed, respectively, at an application rate of about 0.3 pound per acre. No adverse growth effects on cotton plants were observed at such application rate.

The above and other certain active ingredients of the present invention are also found to exhibit selective herbicidal activities at various application rates.

What is claimed is:

1. A herbicidal composition comprising a herbicidal amount of a compound corresponding to the formula:

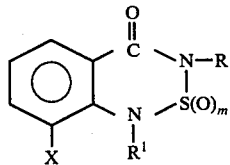

wherein:
X represents —CH$_3$, —OCH$_3$ or CF$_3$;
m represents an integer of 1 or 2;
R represents loweralkyl of 1 to about 6 carbon atoms, haloloweralkyl of 1 to about 6 carbon atoms, alkenyl of 3 to about 6 carbon atoms, haloalkenyl of 3 to about 6 carbon atoms, alkynyl of 3 to about 6 carbon atoms, haloalkynyl of 3 to about 6 carbon atoms, cycloalkyl of 3 to about 8 carbon atoms, unsubstituted phenyl, loweralkylphenyl, halophenyl, benzyl, loweralkylbenzyl, halobenzyl, loweralkoxyloweralkyl of 2 to 6 carbon atoms, diloweralkylaminoloweralkyl of 3 to 10 carbon atoms; loweralkylthioloweralkyl of 2 to 6 carbon atoms, or cyanoloweralkyl of 2 to 7 carbon atoms;
R$^1$ represents hydrogen,

—SO$_2$R$^{10}$ or —SO$_2$NR$^8$R$^9$;
R$^6$ represents loweralkyl and haloloweralkyl having from 1 to 5 carbon atoms, alkenyl and haloalkenyl of 2 to 5 carbon atoms, cycloalkyl of 3 to 6 carbon atoms, loweralkoxyloweralkyl, loweralkylthioloweralkyl, each of 2 to 6 carbon atoms, alkoxycarbonylalkyl of 4 to 8 carbon atoms, phenyl, loweralkylphenyl or halophenyl;
R$^7$ represents alkyl of 1 to 7 carbon atoms, haloalkyl of 1 to 4 carbon atoms, alkenyl and haloalkenyl of 3 to 6 carbon atoms, cycloalkyl of 3 to 6 carbon atoms, phenyl, loweralkylphenyl or halophenyl;
R$^8$ represents loweralkyl of 1 to 4 carbon atoms and cycloalkyl of 3 to 6 carbon atoms;
R$^9$ represents R$^8$ and alkoxy, and when taken together with R$^8$ and the nitrogen from which each depends, a heterocyclic ring of 4 to 8 carbon atoms;
R$^{10}$ represents alkyl and haloalkyl, each of 1 to 7 carbon atoms; and
where R$^1$ is hydrogen, the salts thereof with organic or inorganic bases,
in admixture with a solid or liquid adjuvant.

2. The composition of claim 1 wherein m is 2.
3. The composition of claim 2 wherein R is loweralkyl.
4. The composition of claim 2 wherein R is loweralkyl and R$^1$ is hydrogen.
5. The composition of claim 2 wherein R is loweralkyl and R$^1$ is

6. The composition of claim 2 wherein R is loweralkyl and R$^1$ is hydrogen.
7. The composition of claim 2 wherein R is loweralkyl and R$^1$ is —SO$_2$R$^{10}$.
8. The composition of claim 2 wherein R is 1-methylethyl.
9. The composition of claim 2 wherein X is loweralkyl of from 1 to about 4 carbon atoms.
10. The composition of claim 9 wherein n is 1.
11. The composition of claim 3 wherein X is loweralkyl of from 1 to about 2 carbon atoms, n is 1, and R$^1$ is selected from hydrogen,

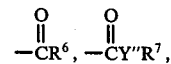

and —SO$_2$R$^{10}$.

12. The composition of claim 11 in which X is in one of the 6, 7 or 8 ring positions.

13. The composition of claim 2 in which the compound is 8-methyl-3-(n-propyl)-1H-2,1,3-benzothiadiazin-4(3H)-one-2,2-dioxide.

14. The composition of claim 2 in which the compound is 8-methyl-3-ethyl-1H-2,1,3-benzothiadiazin-4(3H)-one-2,2-dioxide.

15. The composition of claim 2 in which the compound is 8-methyl-3-(1-methylethyl)-1H-2,1,3-benzothiadiazin-4(3H)-one-2,2-dioxide.

16. The composition of claim 2 in which the compound is 8-methyl-3-(sec. butyl)-1H-2,1,3-benzothiadiazin-4(3H)-one-2,2-dioxide.

17. The composition of claim 2 in which the compound is 3,4-dihydro-8-methyl-3-(1-methylethyl)-4-oxo-1H-2,1,3-benzothiadiazine-1-carboxylic acid, methyl ester, 2,2-dioxide.

18. The composition of claim 2 in which the compound is 3,4-dihydro-8-methyl-3-(1-methylethyl)-4-oxo-1H-2,1,3-benzothiadiazine-1-carboxylic acid, n-propyl ester, 2,2-dioxide.

19. The composition of claim 2 in which the compound is 1-acetyl-8-methyl-3-(1-methylethyl)-1H-2,1,3-benzothiadiazin-4(3H)-one-2,2-dioxide.

20. The composition of claim 2 in which the compound is 8-methyl-3-(1-methylethyl)-1-(1-oxobutyl)-1H-2,1,3-benzothiadiazin-4(3H)-one-2,2-dioxide.

21. The composition of claim 2 in which the compound is 3,4-dihydro-8-methyl-3-(1-methylethyl)-4-oxo-1H-2,1,3-benzothiadiazine-1-carboxylic acid, butyl ester, 2,2-dioxide.

22. The composition of claim 2 in which the compound is 8-methoxy-3-(1-methylethyl)-1H-2,1,3-benzothiadiazin-4(3H)-one-2,2-dioxide.

23. The composition of claim 2 in which the compound is 3,4-dihydro-8-methyl-3-(1-methylethyl)-4-oxo-1H-2,1,3-benzothiadiazine-1-carbothioic acid, S-methyl ester, 2,2-dioxide.

24. The composition of claim 2 in which the compound is 3,4-dihydro-3-methyl-3-(1-methylethyl)-4-oxo-1H-2,1,3-benzothiadiazine-1-carbothioic acid, S-propyl ester, 2,2-dioxide.

25. The composition of claim 2 in which the compound is 8-methyl-3-(1-methylethyl)-1-methylsulfonyl-1H-2,1,3-benzothiadiazin-4(3H)-one-2,2-dioxide.

26. The composition of claim 2 in which the compound is 8-methoxy-3-sec. butyl-1H-2,1,3-benzothiadiazin-4(3H)-one-2,2-dioxide.

27. The composition of claim 2 in which the compound is 8-methoxy-3-n-propyl-1H-2,1,3-benzothiadiazin-4(3H)-one-2,2-dioxide.

28. The composition of claim 2 in which the compound is 8-trifluoromethyl-3-(1-methylethyl)-1H-2,1,3-benzothiadiazin-4(3H)-one-2,2-dioxide.

29. The composition of claim 1 which contains from about 5 to about 95 percent of said compound and the balance at least one substantially inert adjuvant.

30. The composition of claim 2 which contains from about 5 to about 95 percent of said compound and the balance at least one substantially inert adjuvant.

31. The composition of claim 2 in which the compound is 8-methyl-3-(1-methylethyl)-1-propylsulfonyl-1H-2,1,3-benzothiadiazin-4(3H)-one-2,2-dioxide.

32. The composition of claim 2 in which the compound is 8-methyl-3-(1-methylethyl)-1-butylsulfonyl-1H-2,1,3-benzothiadiazin-4(3H)-one-2,2-dioxide.

33. The composition of claim 2 in the form of a wettable powder, a flowable concentrate or an emulsifiable concentrate.

34. A method for selectively controlling undesired plants in the presence of cotton which comprises applying to said plants a herbicidally effective quantity of a compound corresponding to the formula:

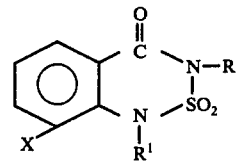

wherein
X is loweralkyl of from 1 to about 4 carbon atoms;
R represents loweralkyl of from 1 to about 6 carbon atoms;
$R^1$ represents hydrogen,

$-SO_2R^{10}$ or $-SO_2NR^8R^9$;
$R^6$ represents loweralkyl and haloloweralkyl having from 1 to 5 carbon atoms, alkenyl and haloalkenyl of 2 to 5 carbon atoms, cycloalkyl of 3 to 6 carbon atoms, loweralkoxyloweralkyl, loweralkylthioloweralkyl, each of 2 to 6 carbon atoms, alkoxycarbonylalkyl of 4 to 8 carbon atoms, phenyl, loweralkylphenyl or halophenyl;
$R^7$ represents alkyl of 1 to 7 carbon atoms, haloalkyl of 1 to 4 carbon atoms, alkenyl and haloalkenyl of 3 to 6 carbon atoms, cycloalkyl of 3 to 6 carbon atoms, phenyl, loweralkylphenyl or halophenyl;
$R^8$ represents loweralkyl of 1 to 4 carbon atoms and cycloalkyl of 3 to 6 carbon atoms;
$R^9$ represents $R^8$ and alkoxy, and when taken together with $R^8$ and the nitrogen from which each depends, a heterocyclic ring of 4 to 8 carbon atoms;
$R^{10}$ represents alkyl and haloalkyl, each of 1 to 7 carbon atoms;
Y" represents a chalcogen group having an atomic number of from 8 to 16 inclusive; and
where $R^1$ is hydrogen, the salts thereof with organic or inorganic bases.

35. The method as in claim 34 in which the compound is one in which $R^1$ is hydrogen, or salts thereof.

36. The method as in claim 34 in which $R^1$ is

37. The method as in claim 34 in which $R^1$ is

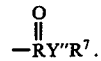

38. The method as in claim 34 in which $R^1$ is $-SO_2R^{10}$.

39. The method as in claim 34 in which R is 1-methylethyl.

40. The method as in claim 34 in which $R^1$ is selected from hydrogen,

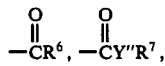

and —SO$_2$R$^{10}$.

41. The method of claim 34 where in the compound is 8-methoxy-3-(1-methylethyl)-1H-2,1,3-benzothiadiazin-4(3H)-one-2,2-dioxide.

42. The method of claim 34 wherein the compound is 3,4-dihydro-8-methyl-3-(1-methylethyl)-4-oxo-1H-2,1,3-benzothiadiazine-1-carbothioic acid, S-methyl ester, 2,2-dioxide.

43. The method of claim 34 wherein the compound is 3,4-dihydro-8-methyl-3-(1-methylethyl)-4-oxo-1H-2,1,3-benzothiadiazine-1-carbothioic acid, S-propyl ester, 2,2-dioxide.

44. The method of claim 34 wherein the compound is 8-methyl-3-(1-methylethyl)-1-methylsulfonyl-1H-2,1,3-benzothiadiazin-4(3H)-one-2,2-dioxide.

45. The method of claim 34 wherein the compound is 8-methyl-3-(1-methylethyl)-1-propylsulfonyl-1H-2,1,3-benzothiadiazin-4(3H)-one-2,2-dioxide.

46. The method of claim 34 wherein the compound is 8-methyl-3-(1-methylethyl)-1-butylsulfonyl-1H-2,1,3-benzothiadiazin-4(3H)-one-2,2-dioxide.

47. The method of claim 34 wherein the compound is 3-(1-methylethyl)-(8-trifluoromethyl)-1H-2,1,3-benzothiadiazin-4(3H)-one-2,2-dioxide.

48. A method for controlling undesired plants which comprises applying to said plants a herbicidally effective quantity of a compound corresponding to the formula:

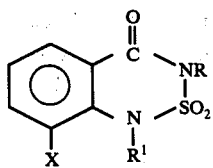

wherein:
X represents —CH$_3$, —OCH$_3$ or —CF$_3$;
R represents loweralkyl of 1 to about 6 carbon atoms, haloloweralkyl of 1 to about 6 carbon atoms, alkenyl of 3 to about 6 carbon atoms, haloalkenyl of 3 to about 6 carbon atoms, alkynyl of 3 to about 6 carbon atoms, haloalkynyl of 3 to about 6 carbon atoms, cycloalkyl of 3 to about 8 carbon atoms, unsubstituted phenyl, loweralkylphenyl, halophenyl, benzyl, loweralkylbenzyl, halobenzyl, loweralkoxyloweralkyl of 2 to 6 carbon atoms, diloweralkylaminoloweralkyl of 3 to 10 carbon atoms; loweralkylthioloweralkyl of 2 to 6 carbon atoms, or cyanoloweralkyl of 2 to 7 carbon atoms;
R$^1$ represents hydrogen,

—SO$_2$R$^{10}$ or —SO$_2$NR$^8$R$^9$;
R$^6$ represents loweralkyl and haloloweralkyl having from 1 to 5 carbon atoms, alkenyl and haloalkenyl of 2 to 5 carbon atoms, cycloalkyl of 3 to 6 carbon atoms, loweralkoxyloweralkyl and loweralkylthioloweralkyl, each of 2 to 6 carbon atoms, alkoxycarbonylalkyl of 4 to 8 carbon atoms, phenyl, loweralkylphenyl or halophenyl;
R$^7$ represents alkyl of 1 to 7 carbon atoms, haloalkyl of 1 to 4 carbon atoms, alkenyl and haloalkenyl of 3 to 6 carbon atoms, cycloalkyl of 3 to 6 carbon atoms, phenyl, loweralkylphenyl or halophenyl;
R$^8$ represents loweralkyl of 1 to 4 carbon atoms and cycloalkyl of 3 to 6 carbon atoms;
R$^9$ represents R$^8$ and alkoxy, and when taken together with R$^8$ and the nitrogen from which each depends, a heterocyclic ring of 4 to 8 carbon atoms;
R$^{10}$ represents alkyl and haloalkyl, each of 1 to 7 carbon atoms; and
where R$^1$ is hydrogen, the salts thereof with organic or inorganic bases.

49. The method as in claim 48 in which one or more compounds of the formula shown are applied in an effective amount of about 0.10 to about 10 pounds per acre.

50. The method as in claim 49 in which one or more of said compounds is applied in total at a rate of about 0.25 to 4 pounds per acre.

51. ThE method as in claim 48 in which R is loweralkyl.

52. The method as in claim 48 in which in the compound R is loweralkyl and R$^1$ is hydrogen, or salts thereof.

53. The method as in claim 48 in which R is loweralkyl and R$^1$ is

54. The method as in claim 48 in which R is loweralkyl and R$^1$ is

55. The method as in claim 48 in which R is loweralkyl and R$^1$ is —SO$_2$R$^{10}$.

56. The method as in claim 48 in which R is 1-methylethyl and X is loweralkyl.

57. The method as in claim 56 in which n is 1.

58. The method as in claim 57 in which X is loweralkyl of from 1 to about 2 carbon atoms, n is 1, and R$^1$ is selected from hydrogen,

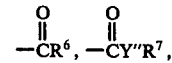

and —SO$_2$R$^{10}$.

59. The method as in claim 57 in which one or more such compounds are applied, in combined total, at an effective rate in the range of about 0.10 to about 10 pounds per acre.

60. The method as in claim 57 in which the rate is in the range of about 0.25 to 4 pounds per acre.

61. The method as in claim 48 in which the compound is 8-methyl-3-(1-methylethyl)-1H-2,1,3-benzothiadiazin-4(3H)-one-2,2-dioxide.

62. The method as in claim 48 in which the compound is 8-methyl-3-(n-propyl)-1H-2,1,3-benzothiadiazin-4(3H)-one-2,2-dioxide.

63. The method as in claim 48 in which the compound is 3,4-dihydro-8-methyl-3-(1-methylethyl)-4-oxo-1H-

2,1,3-benzothiadiazine-1-carboxylic acid, methyl ester, 2,2-dioxide.

64. The method as in claim 48 in which the compound is 3,4-dihydro-8-methyl-3-(1-methylethyl)-4-oxo-1H-2,1,3-benzothiadiazine-1-carboxylic acid, propyl ester, 2,2-dioxide.

65. The method as in claim 48 in which the compound is 8-methyl-3-(1-methylethyl)-1-acetyl-1H-2,1,3-benzothiadiazin-4(3H)-one-2,2-dioxide.

66. The method as in claim 48 in which the compound is 8-methyl-3-(1-methylethyl)-1-(1-oxobutyl)-1H-2,1,3-benzothiadiazin-(4(3H)-one-2,2,-dioxide.

67. The method as in claim 48 in which the compound is 3,4-dihydro-8-methyl-3-(1-methylethyl)-4-oxo-1H-2,1,3-benzothiadiazine-1-carboxylic acid, n-butyl ester, 2,2-dioxide.

68. The method as in claim 48 in which the compound is 8-methoxy-3-(1-methylethyl)-1H-2,1,3-benzothiadiazin-4(3H)-one-2,2-dioxide.

69. The method as in claim 48 in which the compound is 3,4-dihydro-8-methyl-3-(1-methylethyl)-4-oxo-1H-2,1,3-benzothiadiazine-1-carbothioic acid, S-methyl ester, 2,2-dioxide.

70. The method as in claim 48 in which the compound is 3,4-dihydro-8-methyl-3-(1-methylethyl)-4-oxo-1H-2,1,3-benzothiadiazine-1-carbothioic acid, S-propyl ester, 2,2-dioxide.

71. The method as in claim 48 in which the compound is 8-methyl-3-(1-methylethyl)-1-methylsulfonyl-1H-2,1,3-benzothiadiazin-4(3H)-one-2,2-dioxide.

72. The method as in claim 48 in which the compound is 8-methyl-3-sec. butyl-1H-2,1,3-benzothiadiazin-4(3H)-one-2,2-dioxide.

73. The method as in claim 48 in which the compound is 8-methyl-3-(1-methylethyl)-1-propylsulfonyl-1H-2,1,3-benzothiadiazin-4(3H)-one-2,2-dioxide.

74. The method as in claim 48 in which the compound is 8-methyl-3-(1-methylethyl)-1-butylsulfonyl-1H-2,1,3-benzothiadiazin-4(3H)-one-2,2-dioxide.

75. The method as in claim 48 in which the compound is 8-trifluoromethyl-3-(1-methylethyl)-1H-2,1,3-benzothiadiazin-4(3H)-one-2,2-dioxide.

76. The method as in claim 48 in which the compound is 3,4-dihydro-8-methyl-3-(1-methylethyl)-4-oxo-1H-2,1,3-benzothiadiazine-1-carbothioic acid, s-ethyl ester, 2,2-dioxide.

77. A method for selectively controlling undesired plants in the presence of growing soybeans which comprises applying to said plants from about 0.25 to 4 pounds per acre of a compound corresponding to the formula:

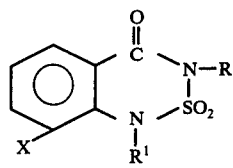

wherein:
X is —CH$_3$, —OCH$_3$ or CF$_3$;
R represents loweralkyl of 1 to about 6 carbon atoms, haloloweralkyl of 1 to about 6 carbon atoms, alkenyl of 3 to about 6 carbon atoms, haloalkenyl of 3 to about 6 carbon atoms, alkynyl of 3 to about 6 carbon atoms, haloalkynyl of 3 to about 6 carbon atoms, cycloalkyl of 3 to about 8 carbon atoms, unsubstituted phenyl, loweralkylphenyl, halophenyl, benzyl, loweralkylbenzyl, halobenzyl, loweralkoxyloweralkyl of 2 to 6 carbon atoms, diloweralkylaminoloweralkyl of 3 to 10 carbon atoms; loweralkylthioloweralkyl of 2 to 6 carbon atoms, or cyanoloweralkyl of 2 to 7 carbon atoms;
R$^1$ represents hydrogen,

—SO$_2$R$^{10}$ or —SO$_2$NR$^8$R$^9$;
R$^6$ represents loweralkyl and haloloweralkyl having from 1 to 5 carbon atoms, alkenyl and haloalkenyl of 2 to 5 carbon atoms, cycloalkyl of 3 to 6 carbon atoms, loweralkoxyloweralkyl, loweralkylthioloweralkyl, each of 2 to 6 carbon atoms, alkoxycarbonylalkyl of 4 to 8 carbon atoms, phenyl, loweralkylphenyl or halophenyl;
R$^7$ represents alkyl of 1 to 7 carbon atoms, haloalkyl of 1 to 4 carbon atoms, alkenyl and haloalkenyl of 3 to 6 carbon atoms, cycloalkyl of 3 to 6 carbon atoms, phenyl, loweralkylphenyl or halophenyl;
R$^8$ represents loweralkyl of 1 to 4 carbon atoms and cycloalkyl of 3 to 6 carbon atoms;
R$^9$ represents R$^8$ alkoxy, and when taken together with R$^8$ and the nitrogen from which each depends, a hetercyclic ring of 4 to 8 carbon atoms;
R$^{10}$ represents alkyl and haloalkyl, each of 1 to 7 carbon atoms; and
where R$^1$ is hydrogen, the salts thereof with organic or inorganic bases.

78. The method of claim 77 in which the said compound is applied at a rate of from about 0.2 to 2 pounds per acre.

79. The method of claim 77 in which R is 1-methylethyl and X is methyl.

* * * * *

UNITED STATES PATENT AND TRADEMARK OFFICE
CERTIFICATE OF CORRECTION

PATENT NO. : 4,116,672
DATED : September 26, 1978
INVENTOR(S) : Lennon H. McKendry et al.

It is certified that error appears in the above-identified patent and that said Letters Patent are hereby corrected as shown below:

Column 1, line 26 "benzothiodiazin" should read -- benzothiadiazin --;

Column 2, line 7 "lowerakyl" should read -- loweralkyl --;

Column 2, line 16 "R$_9$" should read -- R$^9$ --;

Column 3, line 33 "designated" should read -- designates --

Column 3, line 36 "one of more" should read -- one or more --;

Column 5, line 26 "CLBr" should read -- ClBr --;

Column 8, Compound 30 under column heading "Melting Temperature °C" should read -- 147.5-149 --;

Column 9, Compound 69 under column heading "R" should read -- -i-C$_3$H$_7$ --;

Column 12, line 50 insert -- one -- after "(3H)-";

Column 12, line 51 insert -- - -- before "2,2-dioxide";

Column 14, line 28 "loWeralkylphenyl" should read -- loweralkylphenyl --;

Column 15, line 42 "-dihydro-3-" should read -- -dihydro-8- --;

Column 18, line 23 "ThE" should read -- The --;

UNITED STATES PATENT AND TRADEMARK OFFICE
CERTIFICATE OF CORRECTION

PATENT NO. : 4,116,672
DATED : September 26, 1978
INVENTOR(S) : Lennon H. McKendry et al.

It is certified that error appears in the above-identified patent and that said Letters Patent are hereby corrected as shown below:

Column 19, line 13 "2,2,-dioxide" should read -- 2,2-dioxide --;

Column 20, line 43 "$R^8$ alkoxy" should read -- $R^8$ and alkoxy --.

Signed and Sealed this

Sixteenth Day of January 1979

[SEAL]

Attest:

RUTH C. MASON
Attesting Officer

DONALD W. BANNER
Commissioner of Patents and Trademarks